(12) United States Patent
Thompson (10) Patent No.: US 6,438,420 B1
(45) Date of Patent: Aug. 20, 2002

(54) HIGH VOLTAGE SWITCH ISOLATION FOR IMPLANTABLE CARDIOVERTERS/ DEFIBRILLATORS

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/867,097

(22) Filed: May 29, 2001

(51) Int. Cl.$^7$ ................................................ A61N 1/00
(52) U.S. Cl. ............................................................ 607/5
(58) Field of Search ......................................... 607/4, 5

(56) References Cited

U.S. PATENT DOCUMENTS

| | | |
|---|---|---|
| 4,726,380 A | 2/1988 | Vollmann et al. |
| 4,800,883 A | 1/1989 | Winstrom |
| 4,830,006 A | 5/1989 | Haluska et al. |
| 4,850,357 A | 7/1989 | Bach, Jr. |
| 4,880,005 A | 11/1989 | Pless et al. |
| 4,953,551 A | 9/1990 | Mehra et al. |
| 4,998,531 A | 3/1991 | Bocchi et al. |
| 5,117,824 A | 6/1992 | Keimel et al. |
| 5,163,427 A | 11/1992 | Keimel |
| 5,178,140 A | 1/1993 | Ibrahim |
| 5,265,588 A | 11/1993 | Nelson et al. .................. 607/5 |
| 5,292,338 A | 3/1994 | Bardy ............................. 607/5 |

FOREIGN PATENT DOCUMENTS

EP 9218198 10/1992 ............ A61N/1/05

OTHER PUBLICATIONS

Olson et al "Onset and Stability for Ventricular Tachyarrhythmia Detection in an Implantable Pacer–Cardioverter–Defibrillator" Oct. 7–10, 1986 pp. 167–170 Computers in Cardiology, IEEE, Computer Society Press.

Arzbaecher "Automatic Tachycardia Recognition" May–Jun. 1984, pp. 541–547 PACE.

*Primary Examiner*—Scott M. Getzow
(74) *Attorney, Agent, or Firm*—Girma Wolde-Michael (57) ABSTRACT

A battery powered cardioverter or defibrillator employing a DC-DC converter for charging high voltage output capacitors and for delivering biphasic cardioversion or defibrillation pulses through a bridge circuit including high and low side drive circuits under the control of a microprocessor controlled arrhythmia detection system. Upon the detection of an arrhythmia and the selection of cardioversion/defibrillation therapy, the charging of the high voltage output capacitors is commenced and the capacitor voltage enables a regulated voltage source for the high and low side drive circuits for the high power IGTs of each branch of the bridge circuit. High voltage switching transients are suppressed from re-triggering or otherwise affecting operation of the drive circuits. Fail-safe circuitry disables operation of the drive circuits in the event that the first and second control signals are inadvertently provided simultaneously or overlap.

14 Claims, 5 Drawing Sheets

HIGH VOLTAGE SWITCH ISOLATION FOR IMPLANTABLE CARDIOVERTERS/ DEFIBRILLATORS

FIELD OF THE INVENTION

This invention relates to an implantable medical device that delivers sufficient electrical energy to cardiac tissue to defibrillate or cardiovert tachyarrhythmias and thus restore normal sinus rhythm and, more particularly, to improved isolation of drive circuits for controlling discharge of high voltage capacitors providing a biphasic waveform shock.

BACKGROUND OF THE INVENTION

In the field of automatic implantable arrhythmia control devices, the term "cardioversion" or "cardioverter" refers to the process of, and device for, discharging relatively high energy electrical pulses into, or across, cardiac tissue to arrest a life-threatening tachyarrhythmia. Cardioversion pulses may, or may not, be synchronized with a cardiac depolarization or rhythm and may be applied to arrest a malignant ventricular or atrial tachycardia or fibrillation with selectable or programmable pulse energy. The arrest of fibrillation by such pulses is referred to as "defibrillation" (a form of cardioversion), and "defibrillators" have been characterized as a form of cardioverter. In the context of the present invention, it is to be assumed that these terms are interchangeable, and that use of one term is inclusive of the other device or operation, unless specific distinctions are drawn between them. Current devices or implantable devices for the treatment of tachyarrhythmias, provide programmable staged therapies including anti-tachycardia pacing regimens and cardioversion energy and defibrillation energy shock regimens in order to terminate the arrhythmia with the most energy efficient and least traumatic therapies (if possible), as well as single chamber bradycardia pacing therapies. These devices provide a programmable energy, single polarity waveform, and shock from the discharge of a high voltage output capacitor bank through a pair of electrodes disposed in relation to the heart.

Commonly assigned U.S. Pat. No. 5,163,427 to Keimel discloses an implantable cardioverter/defibrillator system, which is capable of providing three defibrillation pulse methods, with a minimum of control and switching circuitry. The output stage is provided with two separate output capacitor banks, which are sequentially discharged during sequential pulse defibrillation and simultaneously discharged during single or simultaneous pulse defibrillation through a two or three electrode system.

Other cardioversion pulse wave shapes have been proposed in conjunction with a variety of electrode systems in order to achieve more efficient cardioversion, including bi-phasic or multi-phasic wave form shocks generated in rapid sequence and applied to the same or separate electrode systems as described in U.S. Pat. Nos. 4,800,833 to Winstrom, 4,830,006 to Haluska et. al., 4,998,531 to Bocchi, 4,953,551 to Mehra, 5,178,140 to Ibrahim, and 4,850,357 to Bach. Despite the additional complexity, it is expected that cardioversion may be achieved more rapidly after the onset of an arrhythmia and at lower current consumption. In order to achieve low current consumption, these stimulation therapy regimens require rapid and efficient charging of high voltage output capacitors from low voltage battery power sources as well as efficient sequential (or simultaneous) discharge of the capacitors through the electrode systems employed.

Generally, it is necessary to employ a DC-DC converter to convert electrical energy from a low voltage, low current power supply to a high voltage energy level stored in a high energy storage capacitor as substantially described in U.S. Pat. No. 5,265,588 and incorporated herein by reference in its entirety. A typical form of DC-DC converter is commonly referred to as a "flyback" converter which employs a transformer having a primary winding in series with the primary power supply and a secondary winding in series with the high energy discharge capacitors. An interrupting circuit or switch is placed in series with the primary coil and battery. Charging of the high-energy capacitors is accomplished by inducing a voltage in the primary winding of the transformer creating a magnetic field in the secondary winding. When the current in the primary winding is interrupted, the collapsing field develops a current in the secondary winding, which is applied to the high energy capacitors to charge them. The repeated interruption of the supply current charges the high-energy capacitors to a desired level over time. Such DC-DC converters are disclosed in the above referenced '427 and '588 patents wherein charging circuits are disclosed which employ flyback oscillator voltage converters which step up the power source voltage and apply charging current to output capacitors until the voltage on the capacitors reaches the programmed shock energy level.

In sequential pulse, multi-phasic systems, two or more output capacitors are charged and discharged through separate discharge circuits arranged in a bridge circuit configuration so that the sequentially generated shocks applied to the same electrode pathway(s) have opposite polarity. The discharge of the high voltage capacitors is typically effected by connecting the charged capacitors to the electrodes in discharge circuit paths through high voltage, high current conducting, Insulated Gate Transistors (IGTs) or metal oxide semiconductor field effect transistors (MOSFETs or power FETs), either employed alone or in electrical series with high voltage thyristers or "triacs". In the above referenced '588, '006, and '427 patents, IGTs or power FETs are switched into conduction by dedicated drive circuits, which respond to low voltage control signals.

These low impedance, high current conducting switches are necessary to make and break the series electrical connection of the high voltage capacitors with the electrode/heart tissue load. The function of these switches must be tightly controlled to assure proper timing of the sequentially generated mono-phasic or biphasic shock impulses and to prevent destruction of the high voltage output circuit by the unintentional insertion of the switches directly across the high voltage capacitors. Noisy switch operation must also be suppressed. In order to electrically isolate the high voltage discharge circuits from the low voltage control circuits and microprocessor based control system, isolation transformers or optical isolators (opto-couplers) or capacitive coupling and common mode rejection circuits have been proposed. In the '006, '357 and '531 patents, transformers are employed to couple discharge control signals to drive circuits. As stated in the '140 patent, such transformers are bulky, and the transformer cores are susceptible to saturation by external magnetic fields.

The optical isolators and driver circuits employed in the '427 patent do not suffer from these drawbacks but still take sizable hybrid circuit volume, are costly, consume battery power, and have potential catastrophic failure modes.

SUMMARY OF THE INVENTION

Accordingly, one aspect of the present invention to provide a highly energy efficient, cost effective and compact circuit for driving high voltage switches in the output circuit of an implantable automatic cardioverter/defibrillator.

Yet another aspect is to provide a driving circuit for the high voltage switches of a cardioversion/defibrillation pulse generator that improves isolation between high and low voltage components and prevents transients from affecting the operation of the switches.

It is a further aspect to provide a cardioversion/defibrillation pulse generator that isolates the battery power supply for the low voltage control system from a separate low voltage power supply for the low voltage drive circuits of the high voltage switches in the high voltage output circuit without the addition of bulky components.

The above aspects and attendant advances are achieved in the context of a battery powered cardioverter or defibrillator employing a DC-DC converter for charging high voltage output capacitors and for delivering biphasic cardioversion or defibrillation pulses through a bridge circuit including high and low side drive circuits under the control of a microprocessor controlled arrhythmia detection system. Upon the detection of an arrhythmia and the selection of cardioversion/defibrillation therapy, the charging of the high voltage output capacitors is commenced and the capacitor voltage enables a regulated voltage source for the high and low side drive circuits for the high power IGTs of each branch of the high voltage bridge output circuit.

Upon reaching full charge, the microprocessor provides first and second, biphasic pulse width defining, control signals in succession to separate inputs of each low side drive circuit which either provide a trigger signal to a high side drive circuit or a gate control signal to a low side IGT so that only one branch of the bridge circuit is enabled for conduction and discharge of the high voltage capacitors through the patient's heart during each phase. The respective high side drive circuit is triggered into producing a high side IGT gate control signal, and both IGTs of the branch are switched rapidly into conduction for the pulse width defined by the duration of the respective control signal.

In accordance with a particular aspect of the invention, high voltage switching transients are suppressed from re-triggering or otherwise affecting operation of the drive circuits. In this regard, discharge circuit means for delivering voltage stored on capacitor means to the heart in a discharge mode of operation and in response to a discharge control signal further comprises high voltage discharge control switch means operable in response to a switching signal for connecting and disconnecting said high voltage capacitor means with the heart for discharging the capacitor means through the heart during the period of connection, voltage regulating means coupled to the capacitor means for sensing the voltage level stored on the capacitor means and for generating a regulated voltage upon charging of the capacitor means to a predetermined voltage level, drive circuit means powered by the regulated voltage and triggerable at an input terminal in response to said discharge control signal for providing the switching signal to the high voltage discharge control switch means, and means for inhibiting transient high voltage signals generated during switching of said high voltage switch means and coupled back to the input terminal of the drive circuit means from re-triggering the drive circuit means.

The inhibiting means preferably comprises monolithic isolation circuitry that uses an isolated output current replicator of an input current in an isolated input current loop. The current replicator comprises an input current loop and an output current loop that are isolated from one another to inhibit high voltage transients in the output current loop during delivery of the cardioversion/defibrillation shock from being reflected or conducted into the input current loop and to the low voltage circuitry potentially causing damage.

The novel elements believed to be characteristic of the present invention are set forth in the appended claims. The invention itself, together with additional objects and attendant advantages, will best be understood by reference to the following detailed description, which, when taken in conjunction with the accompanying drawings, describes a presently preferred embodiment.

BRIEF DESCRIPTION OF THE DRAWINGS

Reference is now made to the accompanying detailed drawings of the preferred embodiments in which like reference numerals represent like or similar parts throughout, and wherein.

DETAILED DESCRIPTION OF THE PREFERRED EMBODIMENT

The present invention relates to the provision of biphasic cardioversion pulses or shocks in a cardioversion system that may or may not also have the capability of providing single or sequential monophasic cardioversion pulses or shocks. In the description of the preferred embodiment that follows, an implantable pacemaker/cardioverter/defibrillator in which the present invention is preferably implemented is capable of providing either single monophasic of biphasic cardioversion pulses or shocks, which only require a pair of cardioversion electrodes. However, a variety of implantable lead and electrode systems may be employed, with more than one cardioversion electrode connected electrically in common to widen the cardioversion energy distribution across the heart. Such electrodes may include indwelling right ventricular, superior vena cava, and coronary sinus electrodes, active pulse generator case electrodes and/or epicardial and subcutaneous patch electrodes in various combinations of two or more.

With a three electrode system, two of the electrodes are connected in common, and the energy distribution between the two common and the third electrode may lead to reduced energy sufficient to reliably cardiovert a heart in fibrillation or high rate malignant ventricular tachycardia.

Figure 1:
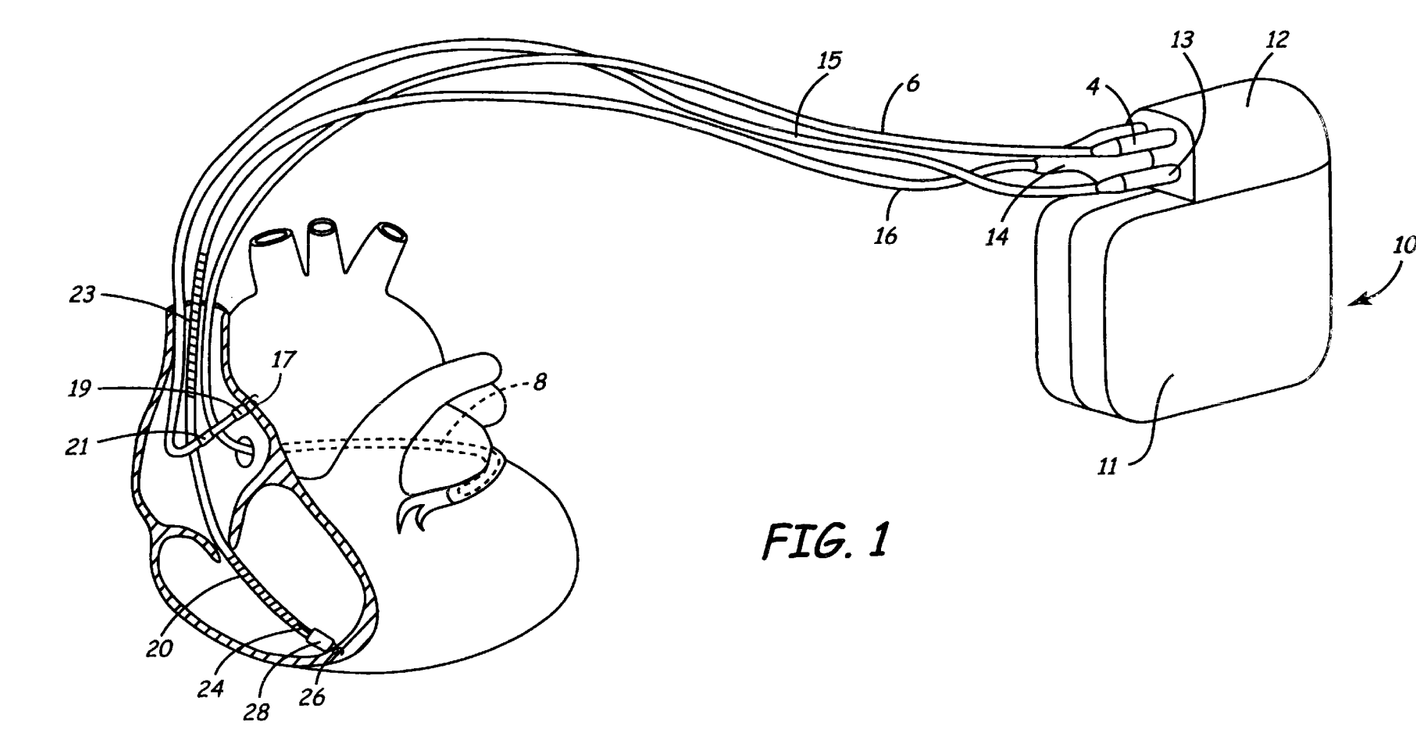
FIG. 1 is a drawing illustrating the physical components of a pacemaker/cardioverter/defibrillator and lead system of the type in which the present invention may be advantageously practiced.

FIG. 1 illustrates a defibrillator and lead set according to the present invention. The ventricular lead is similar to the lead disclosed in U.S. Pat. No. 5,292,338 issued to Bardy, with the addition of a second defibrillation electrode for location in the coronary sinus. The ventricular lead includes an elongated insulative lead body 16, carrying four parallel conductors, mounted within a four-lumen tubular insulative sheath. Located adjacent the distal end of the lead are a ring electrode 24, an extendable helix electrode 26, mounted retractably within an insulative electrode head 28, and an elongated coil electrode 20. An additional elongated coil electrode 23 is located proximal to electrode 20, spaced to allow placement in the right atrium/SVC. Each of the electrodes is coupled to one of the coiled conductors within the lead body 16. Electrodes 24 and 26 are employed for cardiac pacing and for sensing ventricular depolarization.

At the proximal end of the lead is a bifurcated connector 14, which carries four electrical connectors, each coupled to one of the coiled conductors. The defibrillation electrodes 20 and 23 may be fabricated from platinum, platinum alloy or other materials known to be usable in implantable defibrillation electrodes and may conveniently be about 5 cm in length and about 10 cm or greater in length, respectively. The atrial/SVC lead includes an elongated insulative lead body 15, carrying two concentric coiled conductors, separated from one another by a tubular insulative sheath, corresponding to the structure of the commercially available atrial pacing leads. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarization. At the proximal end of the lead is a bipolar, in-line connector 13, which carries two electrical connectors, each coupled to one of the coiled conductors.

The coronary sinus lead takes the form of the coronary sinus lead disclosed in the above cited '338 patent issued to Bardy. The lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4, which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles.

Figure 2:
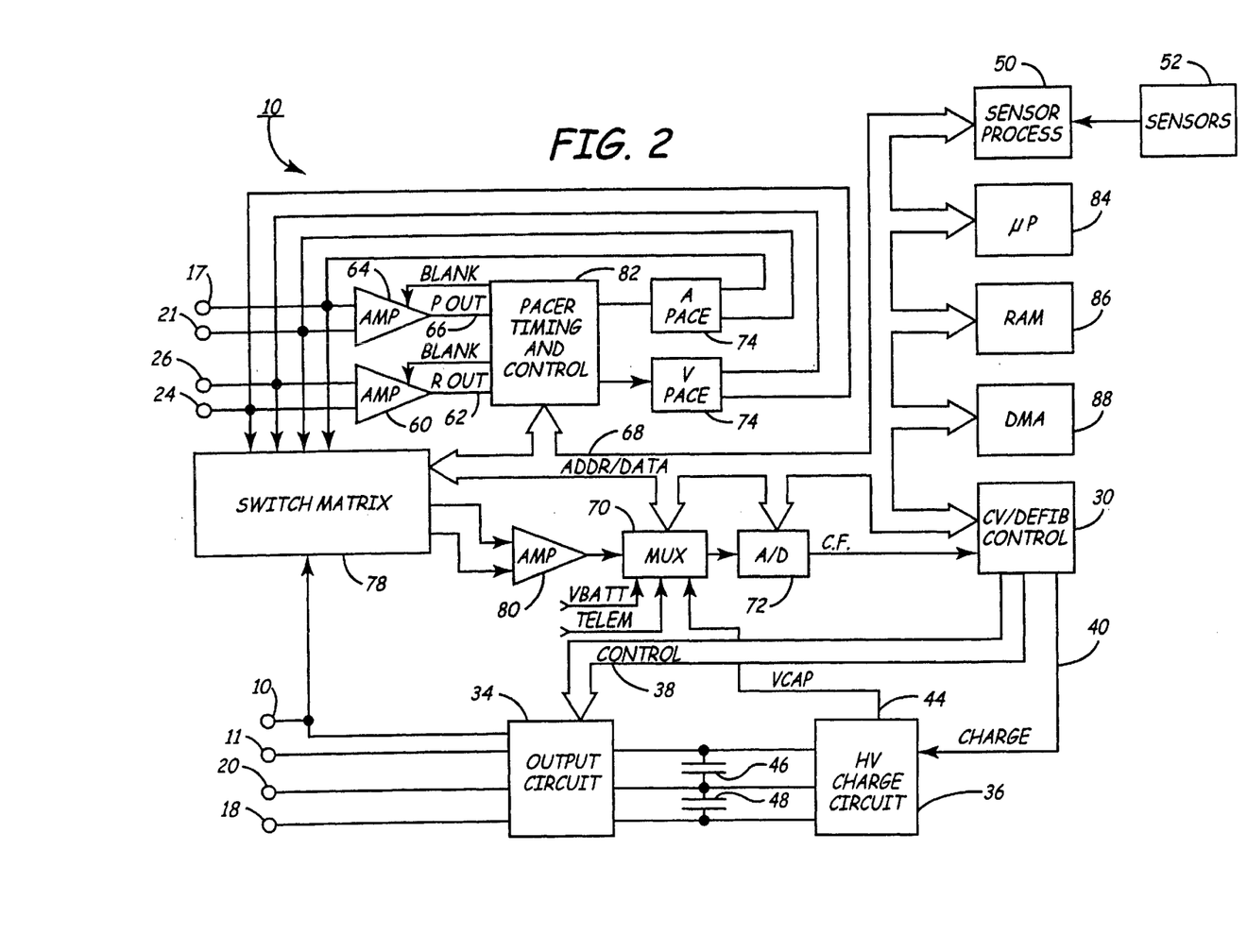
FIG. 2 is a functional block diagram illustrating the interconnection of the improved voltage conversion circuitry of the present invention with the primary functional components of an implantable pacemaker/cardioverter/defibrillator.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including cardioverter and defibrillators which do not provide anti-tachycardia pacing therapies.

The device as illustrated is provided with an electrode system including electrodes as illustrated in FIG. 1. Optional electrode 11 is the uninsulated portion of the housing of the implantable pacemaker/cardioverter/defibrillator 10. Electrode 20 is a defibrillation electrode located in the right ventricle. Electrode 11 is located in the right atrium and SVC. Electrode 18 is a defibrillation electrode located in the coronary sinus and great vein. Electrodes 24 and 26 are used for sensing and pacing in the ventricle. Electrodes 17 and 21 are used for pacing and sensing in the atrium.

Electrodes 10, 11, 18 and 20 are coupled to high voltage output circuit 34. High voltage output circuit 34 includes high voltage switches controlled by CV/defibrillator control logic 30 via control bus 38. The switches within circuit 34 control which electrodes are employed and which are coupled to the positive and negative terminals of the capacitor bank including capacitors 46 and 48 during delivery of the defibrillation pulses. Capacitors 46 and 48 are charged up to a pre-programmed regulated voltage via HV charge circuit 36, Vcop signal 44 and CV/defibrillator control circuit 30 as substantially described in the '427 patent incorporated herein by reference in its entirety.

Electrodes 24 and 26 are located on or in the ventricle and are coupled to the R-wave amplifier 60, which preferably takes the form of an automatic gain controlled amplifier providing an adjustable sensing threshold as a function of the measured R-wave amplitude. A signal is generated on R-out line 62 whenever the signal sensed between electrodes 24 and 26 exceeds the present sensing threshold.

Electrodes 17 and 21 are located on or in the atrium and are coupled to the P-wave amplifier 64, which preferably also takes the form of an automatic gain controlled amplifier providing an adjustable sensing threshold as a function of the measured P-wave amplitude. A signal is generated on P-out line 66 whenever the signal sensed between electrodes 17 and 21 exceeds the present sensing threshold. The general operation of the R-wave and P-wave amplifiers 60 and 64 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 78 is used to select which of the available electrodes are coupled to wide band (0.5–200 Hz) amplifier 80 for use in digital signal analysis. Selection of electrodes is controlled by the microprocessor 84 via data/address bus 68, which selections may be varied as desired. Signals from the electrodes selected for coupling to bandpass amplifier 80 are provided to multiplexer 70, and thereafter converted to multi-bit digital signals by A/D converter 72, for storage in random access memory 86 under control of direct memory access circuit 88. Microprocessor 84 may employ digital signal analysis techniques to characterize the digitized signals stored in random access memory 86 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus for accomplishing pacing, cardioversion and defibrillation functions is as follows. The pacer timing/control circuitry 82 includes programmable digital counters which control the basic time intervals associated with DDD, VVI, DVI, VDD, AAI, DDI and other modes of single and dual chamber pacing well known to the art. Circuitry 82 also controls escape intervals associated with anti-tachyarrhythmia pacing in both the atrium and the ventricle, employing any anti-tachyarrhythmia pacing therapies known to the art.

Intervals defined by pacing circuitry 82 include atrial and ventricular pacing escape intervals and the refractory periods during which sensed P-waves and R-waves are ineffective to restart timing of the escape intervals and the pulse widths of the pacing pulses. The durations of these intervals are determined by microprocessor 84, in conjunction with various sensors 52 and sensor processing circuitry 50 as is well known in the art, in response to stored data in memory 86 and are communicated to the pacing circuitry 82 via address/data bus 68. Pacer circuitry 82 also determines the amplitude of the cardiac pacing pulses under control of microprocessor 84.

During pacing, the escape interval counters within pacer timing/control circuitry 82 are reset upon sensing of R-waves and P-waves as indicated by signals on lines 62 and 66, and in accordance with the selected mode of pacing on timeout trigger generation of pacing pulses by pacer output circuitry 74 and 76, which are coupled to electrodes 17, 21, 24 and 26. The escape interval counters are also reset on generation of pacing pulses, and thereby control the basic timing of cardiac pacing functions, including anti-tachyarrhythmia pacing. The durations of the intervals defined by the escape interval timers are determined by microprocessor 84, via data/address bus 68. The value of the count present in the escape interval counters when reset by sensed R-waves and P-waves may be used to measure the durations of R-R intervals, P-P intervals, P-R intervals and R-P intervals, which measurements are stored in memory 86 and used to detect the presence of tachyarrhythmias.

Microprocessor 84 operates as an interrupt driven device, and is responsive to interrupts from pacer timing/control circuitry 82 corresponding to the occurrence sensed P-waves and R-waves and corresponding to the generation of cardiac pacing pulses. These interrupts are provided via data/address bus 68. Any necessary mathematical calculations to be performed by microprocessor 84 and any updating of the values or intervals controlled by pacer timing/control circuitry 82 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored.

Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 86 is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et at, all incorporated herein by reference in their entireties.

An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated herein in its entirety. Atrial fibrillation detection methodologies, in particular, are disclosed in Published PCT Application Serial No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference in their entireties. In the context of the present invention, however, the specific methodology employed to detect fibrillation is not critical.

Figure 3:
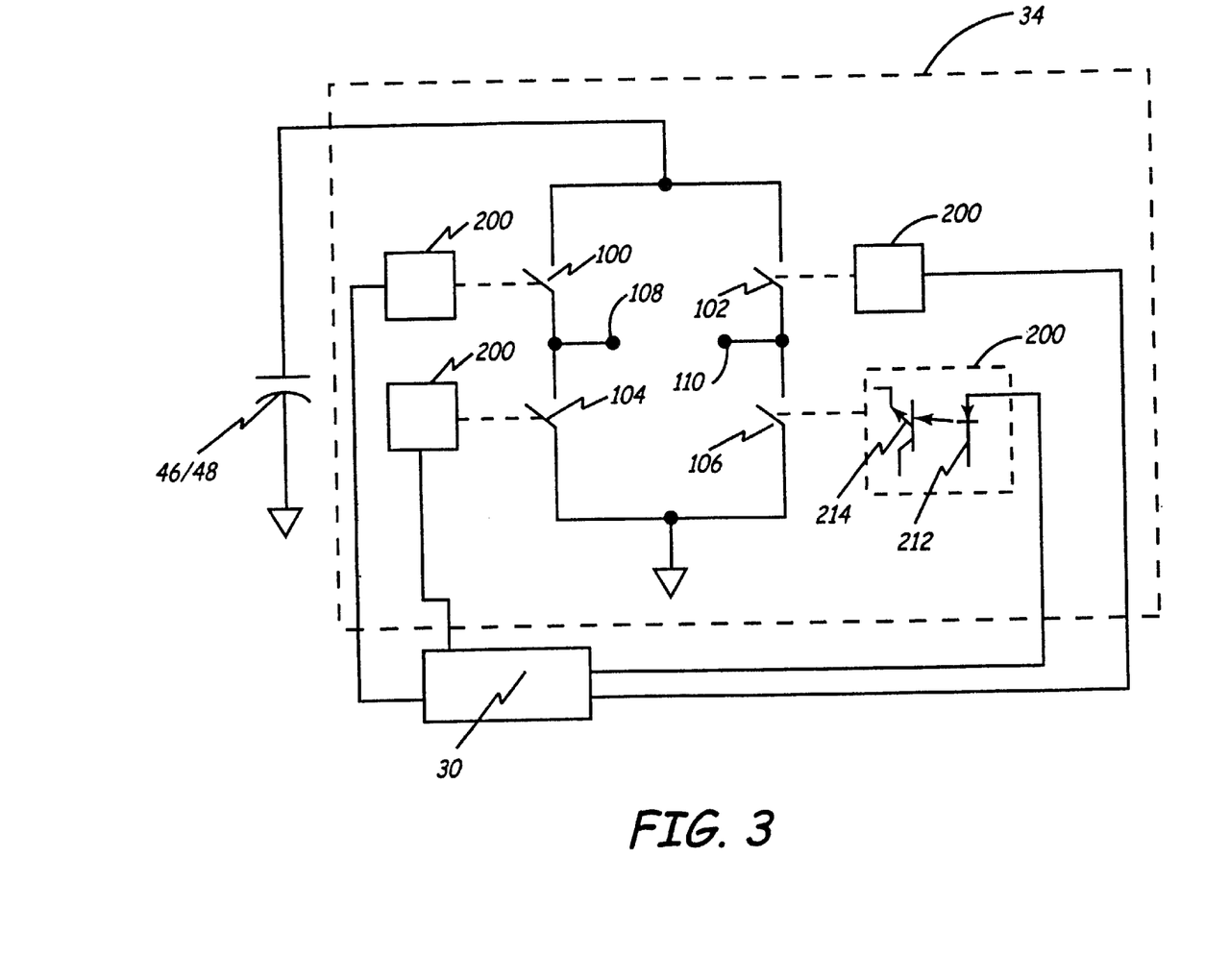
FIG. 3 is a schematic diagram of a preferred embodiment of the pacemaker/cardioverter/defibrillator employing a high voltage switching and control circuit.
Figure 4:
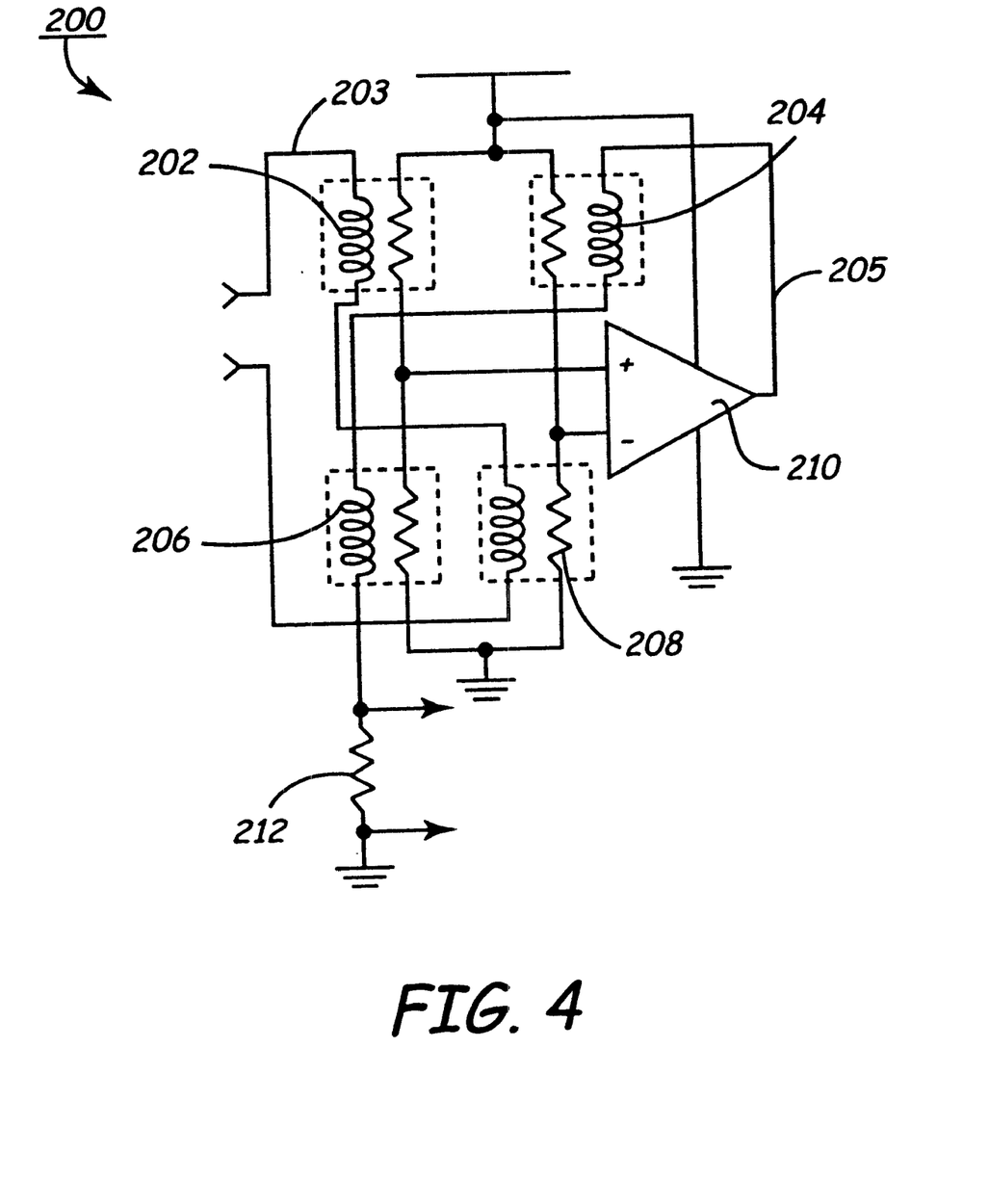
FIG. 4 is an electrical schematic diagram of an isolation circuit of the present invention employed in FIG. 3.

The best mode of practicing the present invention known to the inventor is illustrated in conjunction with the design of a pacemaker/cardioverter/defibrillator employing the major circuit components depicted in FIG. 2 and the specific circuits of FIGS. 3 and 4. The present invention constitutes improvement in the voltage output circuitry for generating cardioversion shocks and may be practiced in connection with any cardioverter or defibrillator design. The particular circuitry involved in the implementation of the voltage output circuitry and further circuitry, which supplies signals to operate the output circuitry, are shown in specific detail.

FIG. 3 is a simplified exemplary prior art design of an implantable cardioverter having circuitry for generating high energy cardioversion and defibrillation pulses and showing low voltage circuitry controlling high voltage switches as substantially described in U.S. Pat. No. 5,163, 427, incorporated here-in by reference in its entirety. The output circuitry 34 (switches 100, 102, 104, and 106 (power FET, IGT, triacs, or the like) and isolation circuits 200) are so configured that they may provide simultaneous pulse, multiple electrode; sequential pulse, multiple electrode; or single pulse, two electrode defibrillation and/or cardioversion pulse regimens delivered through high voltage leads 208 and 210. The output circuitry is configured to allow delivery of energy (high voltage charge circuitry not shown in FIG. 3) sequentially from two capacitor banks (46 and 48) during sequential pulse regimens and to deliver the energy stored in both capacitor banks (46/48) simultaneously during simultaneous pulse, multiple electrode and single pulse, two electrode defibrillation pulse regimens. Isolation between low voltage control circuitry 30 and high voltage switching circuitry 34 is provided by opto-isolators 200 (LED 212/ photo transistor 214), 1 shown in detail.

Opto-isolators and transformers are typically non-monolithic and require DC and low frequency signals be converted to AC before being passed through the isolation device. It is not practical to fully integrate these devices and furthermore the isolators are often slow and difficult to interface with other circuitry. The concept described herein below overcomes these obstacles and limitations with the addition of a couple of thin film and insulating layers to a standard IC (CMOS or Bipolar) process.

Figure 5:
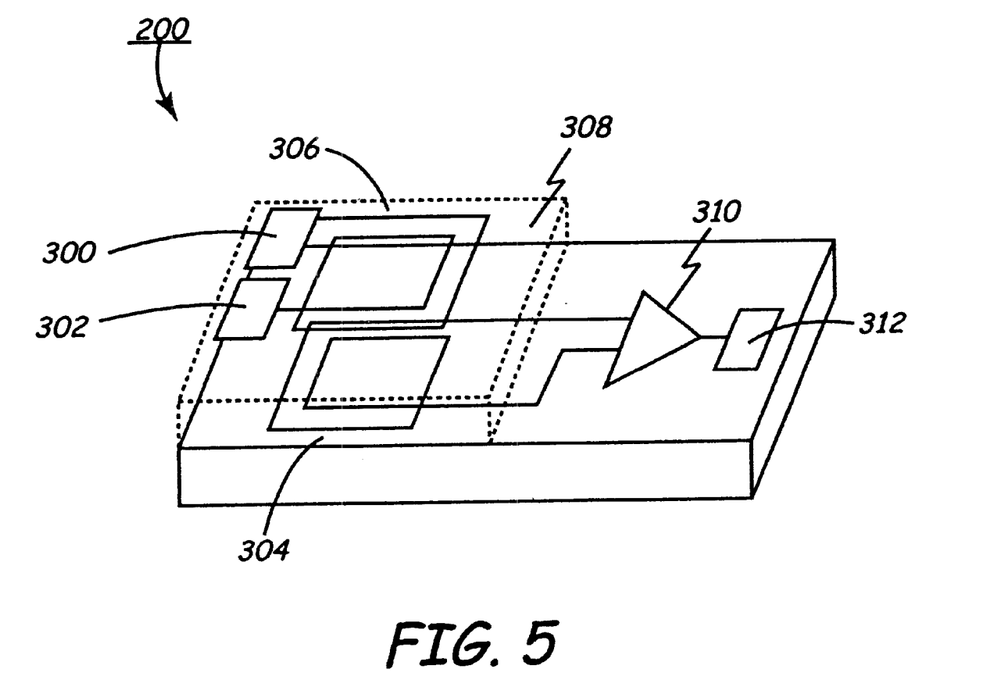
FIG. 5 is an alternative embodiment diagram of an isolation circuit of the present invention employed in FIG. 3.

FIGS. 4 and 5 illustrate two alternative embodiments of drive circuits of the present invention that may be substituted for the conventional opto-isolators or transformers. Each drive circuit is responsive to an input current signal for providing a switching signal to the a respective one of the high voltage switches 100, 102, 104 or 106 in the above-described sequence after the high voltage output capacitor is charged to the predetermined voltage level. In each case, an input current loop and an output current loop are formed as an integrated circuit isolated from one another to inhibit high voltage transients in the output current loop during delivery of the cardioversion/defibrillation shock from being coupled back into the input current loop, whereby the switching signal is generated in the output current loop when the input current signal is applied to the input current loop.

FIG. 4 describes a monolithic isolation circuit 200 that uses an isolated output current replicator of a current in an isolated input current loop 201. The design utilizes four magnetically field sensitive resistors (202, 204, 206, and 208) in a bridge configuration in conjunction with preferably two on-chip current loops 203 and 205 and a conventional operational amplifier 210. Regulated supply 207 is derived from the high voltage charge circuit 36. The resistors 202, 204, 206, and 208 are formed of giant magneto-resistive (GMR) material that displays a high magnetic sensitivity and is easily incorporated into a conventional integrated circuit (IC) processes. The input and output current carrying conductors 203 and 205 placed over the magnetic field sensitive resistors generate the cross-coupled magnetic fields. The input current is counterbalanced by an isolated equal feedback current loop (through resistors 204 and 206) from the op amp 210. The output current through resistor 212 provides the switching signal to the high voltage circuitry/switches 101/102/104/106 of FIG. 3.

In FIG. 4, each GMR resistor has a first resistance in the absence of an input current signal and a second resistance when an input current signal is applied to the input current carrying conductor. The input current loop is thus formed of an input current carrying IC conductor 203 formed on an IC substrate. First and second giant magneto-resistive resistors 202 and 208 are situated with respect to and electrically isolated from the input current carrying conductor 203. The output current loop is formed of a second current carrying conductor 205 on the IC substrate. Third and fourth GMR resistors 204 and 206 are situated with respect to and electrically isolated from the second current carrying conductor 205. The operational amplifier 210 formed on the IC has a first amplifier input coupled to the first and third giant GMR resistors 202 and 208, a second amplifier input coupled to the second and fourth GMR resistors 204 and 206, and an amplifier output coupled to the output current carrying conductor 205.

The operational amplifier 210 emits an output current signal on the output current carrying conductor 205 that generates the switching signal across resistor 212 when the first and second GMR resistors 202 and 208 are changed in resistance by the input current signal. The output current signal also then switches the resistance of the third and fourth GMR resistors, which turns off the operational amplifier 210 and terminates the output current signal and switching signal.

FIG. 5 describes a monolithic isolation circuit 200 that uses an isolated output current 304 replicator of a current in an isolated input current loop 306. The low voltage circuitry input is 300 and 302, which causes a current to flow in a micro-electrical mechanical (MEMs) fabricated low-loss input coil 306. An insulation layer 308 isolates the input coil 306 from an output coil 304 fabricated with conventional IC fabrication techniques. Operational amplifier 310 amplifies the input signal and provides this signal to the high voltage circuitry/switches via output 312. This design includes a 2500-volt standoff and transmission rates up to 100 Mbits/second at a reduced power level over optical methods. Again, this technology could be integrated on top of a standard CMOS wafer allowing similar advantages as described above.

Both embodiments would be integrated over the top of standard CMOS processes, would substantially reduce hybrid volume (no, or reduced area interface IC, no/reduced number of high voltage components), hybrid costs (FAPC) and improved reliability and patient safety over conventional methods for the isolation of the high voltage output circuitry from low voltage control circuitry.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications and alterations should therefore be seen within the scope of the present invention.

What is claimed is:

1. A cardioverter/defibrillator for delivering cardioversion/defibrillation shocks from the discharge of at least one high voltage output capacitor through a cardioversion/defibrillation lead to a patient's heart comprising:

a power supply; a DC-DC converter coupled to the power supply for the charging the high voltage output capacitor to a predetermined voltage level;

high voltage discharge switch means coupled between the high voltage output capacitor and the cardioversion/defibrillation lead for discharging the high voltage output capacitor to deliver the cardioversion/defibrillation shock in response to a switching signal;

means for generating an input current signal following charging the high voltage output capacitor to the predetermined voltage level; and drive circuit means responsive to the input current signal for providing said switching signal after the high voltage output capacitor is charged to the predetermined voltage level further comprising monolithic isolation circuit means comprising an input current loop and an output current loop that are formed as an integrated circuit isolated from one another to inhibit high voltage transients in the output current loop during delivery of the cardioversion/defibrillation shock from being coupled back into the input current loop, whereby the switching signal is generated in the output current loop when the input current signal is applied to the input current loop.

2. The cardioverter/defibrillator of claim 1, wherein the high voltage output circuit is discharged through a plurality of the high voltage discharge switch means arranged in a high side and low side bridge to deliverer biphasic cardioversion/defibrillation pulses in response to switching signals provided by a like plurality of drive circuit means.

3. The cardioverter/defibrillator of claim 2, wherein:

the input current loop is formed of an input current carrying conductor on an integrated circuit substrate;

at least one giant magneto-resistive resistor is situated with respect to and electrically isolated from the input current carrying conductor that has a first resistance in the absence of an input current signal and a second resistance when an input current signal is applied to the input current carrying conductor;

the output current loop is formed of an output current carrying conductor on the integrated circuit substrate; and further comprising replicating circuit means coupled to the at least one giant magneto-resistive resistor and the output current carrying conductor for replicating the input current signal to form the switching signal in the output current loop when the magneto-resistive element is changed in resistance by the input current signal.

4. The cardioverter/defibrillator of claim 3, wherein the replicating circuit means comprises an operational amplifier having an amplifier input coupled to said giant magneto-resistive resistor and an amplifier output coupled to said output current carrying loop.

5. The cardioverter/defibrillator of claim 2, wherein:
the input current loop is formed of an input current carrying conductor on an integrated circuit substrate;
first and second giant magneto-resistive resistors are situated with respect to and electrically isolated from the input current carrying conductor, each giant magneto-resistive resistor having a first resistance in the absence of an input current signal and a second resistance when an input current signal is applied to the input current carrying conductor;
the output current loop is formed of a second current carrying conductor on the integrated circuit substrate;
third and fourth giant magneto-resistive resistors are situated with respect to and electrically isolated from the second current carrying conductor, each giant magneto-resistive resistor having a first resistance in the absence of an input current signal and a second resistance when an output current signal is present on the output current carrying conductor; and
an operational amplifier formed on the integrated circuit having a first amplifier input coupled to the first and third giant magneto-resistive elements, a second amplifier input coupled to the second and fourth giant magneto-resistive element, and an amplifier output coupled to the output current carrying conductor, whereby the input current signal on the input current carrying conductor is replicated to form the switching signal in the output current loop when the first and second magneto-resistive elements are changed in resistance by the input current signal.

6. The cardioverter/defibrillator of claim 1, wherein:
the input current loop is formed of an input current carrying conductor on an integrated circuit substrate;
at least one giant magneto-resistive resistor is situated with respect to and electrically isolated from the input current carrying conductor that has a first resistance in the absence of an input current signal and a second resistance when an input current signal is applied to the input current carrying conductor;
the output current loop is formed of an output current carrying conductor on the integrated circuit substrate; and
further comprising replicating circuit means coupled to the at least one giant magneto-resistive resistor and the output current carrying conductor for replicating the input current signal to form the switching signal in the output current loop when the magneto-resistive element is changed in resistance by the input current signal.

7. The cardioverter/defibrillator of claim 6, wherein the replicating circuit means comprises an operational amplifier having an amplifier input coupled to said giant magneto-resistive resistor and an amplifier output coupled to said output current carrying loop.

8. The cardioverter/defibrillator of claim 1, wherein:
the input current loop is formed of an input current carrying conductor on an integrated circuit substrate; and
first and second giant magneto-resistive resistors are situated with respect to and electrically isolated from the input current carrying conductor, each giant magneto-resistive resistor having a first resistance in the absence of an input current signal and a second resistance when an input current signal is applied to the input current carrying conductor;
the output current loop is formed of a second current carrying conductor on the integrated circuit substrate;
third and fourth giant magneto-resistive resistors are situated with respect to and electrically isolated from the second current carrying conductor, each giant magneto-resistive resistor having a first resistance in the absence of an input current signal and a second resistance when an output current signal is present on the output current carrying conductor; and
an operational amplifier formed on the integrated circuit having a first amplifier input coupled to the first and third giant magneto-resistive elements, a second amplifier input coupled to the second and fourth giant magneto-resistive element, and an amplifier output coupled to the output current carrying conductor, whereby the input current signal on the input current carrying conductor is replicated to form the switching signal in the output current loop when the first and second magneto-resistive elements are changed in resistance by the input current signal.

9. The cardioverter/defibrillator of claim 1, wherein:
the input current loop comprises a low loss conductor coil formed on a first side of an insulation layer of an integrated circuit by micro-electrical mechanical fabrication; and
the output current loop comprises a low loss conductor coil formed on a second side of an insulation layer of an integrated circuit by micro-electrical mechanical fabrication.

10. The cardioverter/defibrillator of claim 9, wherein the high voltage output circuit is discharged through a plurality of the high voltage discharge switch means arranged in a high side and low side bridge to deliverer biphasic cardioversion/defibrillation pulses in response to switching signals provided by a like plurality of drive circuit means.

11. A high voltage isolation circuit for isolating input and output circuitry of an implantable medical device comprising:
an input current loop formed of an input current carrying conductor on an integrated circuit substrate;
at least one giant magneto-resistive resistor situated with respect to and electrically isolated from the input current carrying conductor that has a first resistance in the absence of an input current signal and a second resistance when an input current signal is applied to the input current carrying conductor;
an output current loop formed of an output current carrying conductor on the integrated circuit substrate; and
replicating circuit means coupled to the at least one giant magneto-resistive resistor and the output current carrying conductor for replicating the input current signal to form an output signal in the output current loop when the magneto-resistive element is changed in resistance by the input current signal.

12. The high voltage isolation circuit of claim 11, wherein the replicating circuit means comprises an operational amplifier having an amplifier input coupled to said giant magneto-resistive resistor and an amplifier output coupled to said output current carrying loop.

13. A high voltage isolation circuit for isolating input and output circuitry of an implantable medical device comprising:
- an input current loop formed of an input current carrying conductor on an integrated circuit substrate;
- first and second giant magneto-resistive resistors situated with respect to and electrically isolated from the input current carrying conductor, each giant magneto-resistive resistor having a first resistance in the absence of an input current signal and a second resistance when an input current signal is applied to the input current carrying conductor;
- an output current loop formed of a second current carrying conductor on the integrated circuit substrate;
- third and fourth giant magneto-resistive resistors situated with respect to and electrically isolated from the second current carrying conductor, each giant magneto-resistive resistor having a first resistance in the absence of an input current signal and a second resistance when an output current signal is present on the output current carrying conductor; and
- an operational amplifier formed on the integrated circuit having a first amplifier input coupled to the first and third giant magneto-resistive elements, a second amplifier input coupled to the second and fourth giant magneto-resistive element, and an amplifier output coupled to the output current carrying conductor, whereby the input current signal on the input current carrying conductor is replicated to form the output signal in the output current loop when the first and second magneto-resistive elements are changed in resistance by the input current signal.

14. A high voltage isolation circuit for isolating input and output circuitry of an implantable medical device comprising:
- a low loss conductor coil formed on a first side of an insulation layer of an integrated circuit by micro-electrical mechanical fabrication; and
- a low loss conductor coil formed on a second side of an insulation layer of an integrated circuit by micro-electrical mechanical fabrication.

\* \* \* \* \*